(12) United States Patent
Singh et al.

(10) Patent No.: US 8,158,607 B2
(45) Date of Patent: Apr. 17, 2012

(54) CRYSTALLINE FORM OF LAMIVUDINE

(75) Inventors: Girij Pal Singh, Pune (IN); Dhananjai Srivastava, Pune (IN); Manmeet Brijkishore Saini, Pune (IN); Pritesh Rameshbhai Upadhyay, Pune (IN)

(73) Assignee: Lupin Limited, Mumbai (IN)

( * ) Notice: Subject to any disclaimer, the term of this patent is extended or adjusted under 35 U.S.C. 154(b) by 480 days.

(21) Appl. No.: 12/297,174

(22) PCT Filed: Feb. 9, 2007

(86) PCT No.: PCT/IN2007/000047
§ 371 (c)(1),
(2), (4) Date: Oct. 14, 2008

(87) PCT Pub. No.: WO2007/119248
PCT Pub. Date: Oct. 25, 2007

(65) Prior Publication Data
US 2009/0281053 A1 Nov. 12, 2009

(30) Foreign Application Priority Data
Apr. 18, 2006 (IN) .............................. 347/KOL/2006

(51) Int. Cl.
*A01N 43/58* (2006.01)
*A61K 31/50* (2006.01)
*A61K 31/70* (2006.01)
*C07D 239/00* (2006.01)
*C07D 239/02* (2006.01)

(52) U.S. Cl. ............................ 514/50; 544/242; 514/247

(58) Field of Classification Search .................. None
See application file for complete search history.

(56) References Cited

U.S. PATENT DOCUMENTS
5,047,407 A 9/1991 Belleau
5,905,082 A 5/1999 Roberts et al.

FOREIGN PATENT DOCUMENTS
EP 0517145 12/1992
WO 9117159 11/1991

OTHER PUBLICATIONS (R) M. J. O'Neil et al. (eds.), "The Merck Index, 13th Edition," Merck & Co., Whitehouse Station, NJ, 2001, only pp. 958-959 supplied (see entry "5367," Lamivudine).*
Harris, R. K. et al., ""Polymorphism" in a novel anti-viral agent: Lamivudine," J. Chem. Soc., Perkin Trans. 2, vol. 12, 1997, pp. 2653-2659 (XP002432450).
Jozwiakowski, M. J., "Solubility Behaviour of Lamivudine Crystal Forms in Recrystallisation Solvents," Journal of Pharmaceutical Sciences, American Pharmaceutical Association, Washington, US, vol. 85, No. 2, Feb. 1996, pp. 193-199 (XP-002210585).
Lachman et al., "The Theory and Practice of Industrial Pharmacy," Third Ed., Varghese Publishing House, Bombay, (1987) pp. 317.
International Preliminary Report on Patentabililty issued in PCT Application No. PCT/IN2007/000047, dated Oct. 21, 2008.

* cited by examiner

*Primary Examiner* — Lawrence E Crane
(74) *Attorney, Agent, or Firm* — Leydig, Voit & Mayer, Ltd.

(57) ABSTRACT

The disclosure herein relates to a new Lamivudine polymorphic form, methods of making the same, and pharmaceutical formulations thereof. A (−) cis-4-amino-1-(2-hydroxymethyl-1,3-oxathiolan-5-yl)-(1H)-pyrimidin-2-one in the form of monoclinic crystals has characteristic powder X-ray diffractogram, as disclosed herein, is disclosed along with a process for preparation of the same. A pharmaceutical composition in solid dosage unit form comprising a therapeutically effective amount of a new Lamivudine polymorphic form in combination with a pharmaceutically acceptable carrier is also disclosed along with a pharmaceutical composition useful for treating HIV infections in humans.

39 Claims, 16 Drawing Sheets

Figure 1:
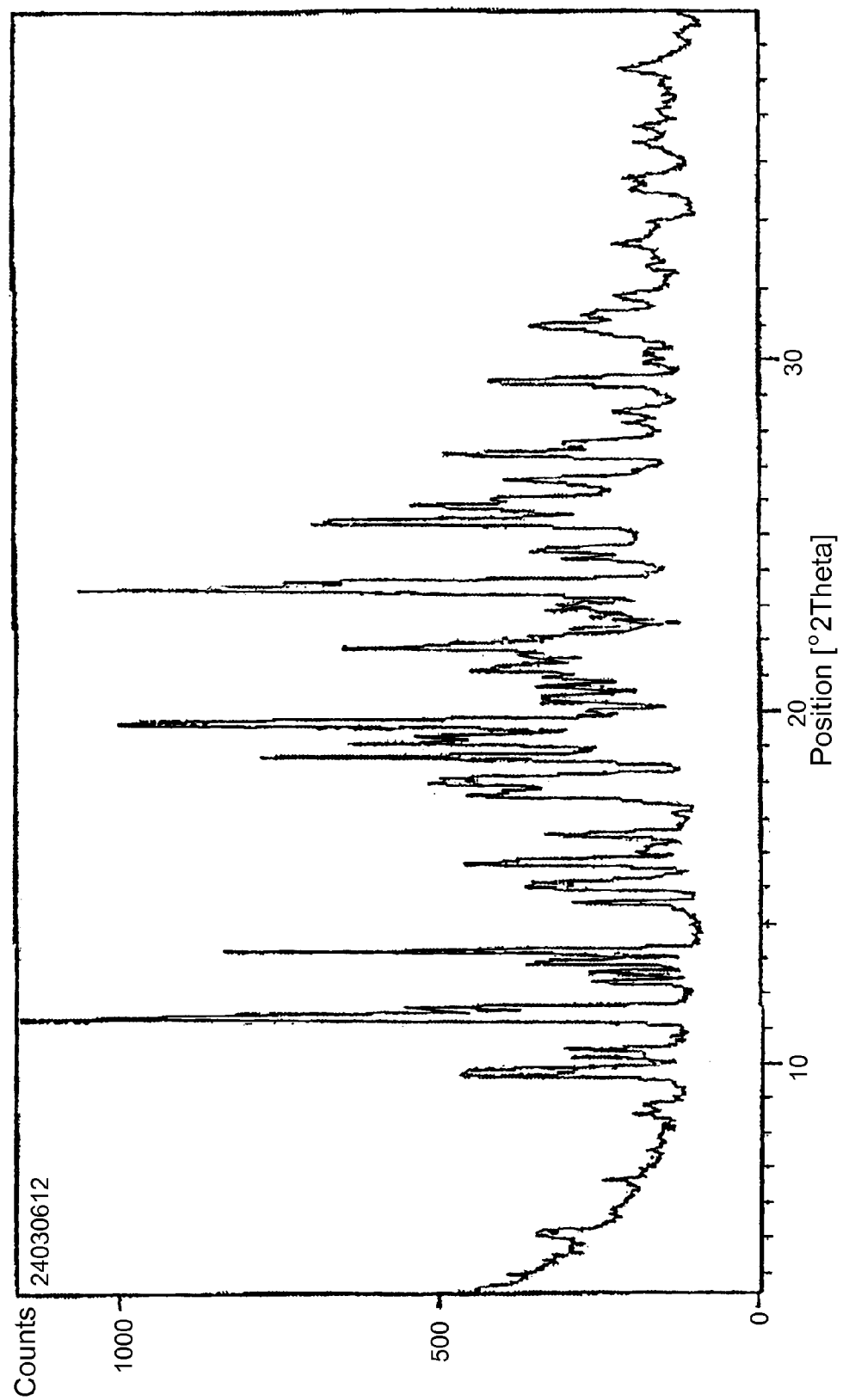

FIG. 16
a
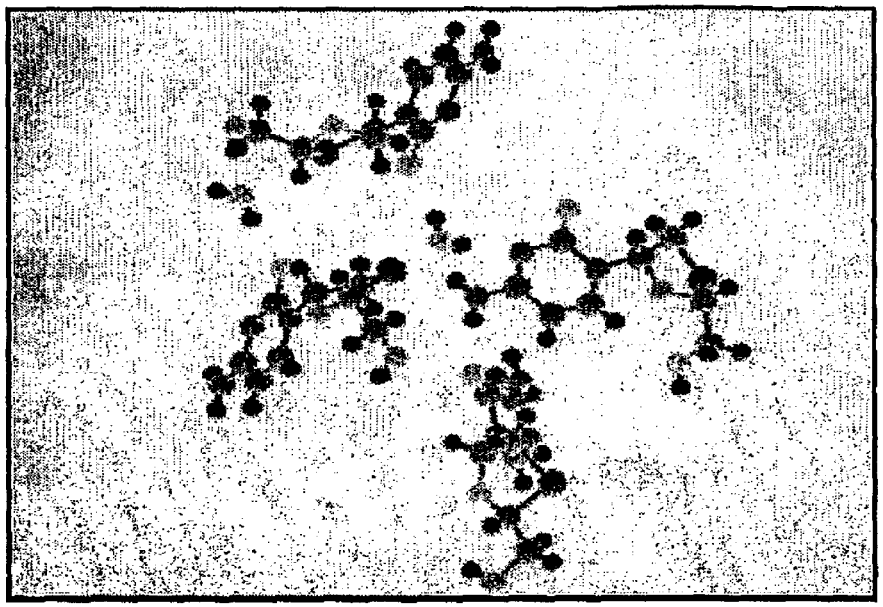
b
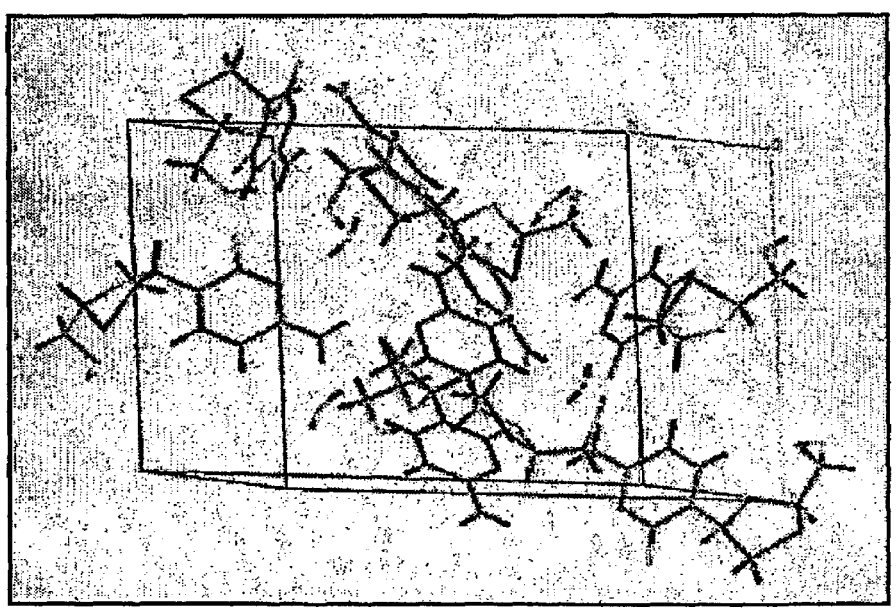

CRYSTALLINE FORM OF LAMIVUDINE

CROSS-REFERENCE TO RELATED APPLICATIONS

This patent application is a U.S. National Phase of International Patent Application No. PCT/IN2007/000047, filed Feb. 9, 2007, which claims the benefit of India Patent Application No. 347/KOL/2006, filed Apr. 18, 2006, each of which are incorporated herein by reference in their entireties.

FIELD OF INVENTION

The present invention relates to a new Lamivudine polymorphic form, pharmaceutical formulations thereof.

BACKGROUND OF THE INVENTION

Lamivudine (I) (CAS No. 134678-17-4) is chemically known as (2R-cis)-4-amino-1-[2-(hydroxymethyl)-1,3-oxathiolan-5-yl]-2(1H)-pyrimidinone, also known as (−) cis-4-amino-1-(2-hydroxymethyl-1,3-oxathiolan-5-yl)-(1H)-pyrimidin-2-one

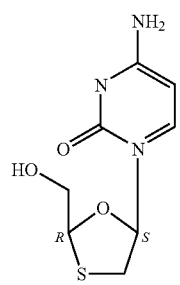

(I)

Lamivudine is a reverse transcriptase inhibitor used in the treatment of HIV infection alone or in combination with other class of Anti HIV drugs.

Lamivudine is commercially available in a pharmaceutical composition under the brand name EPIVIR® marketed by GlaxoSmithKine and is covered under U.S. Pat. No. 5,047,407.

U.S. Pat. No. 5,047,407 claims 1,3-oxathiolane derivatives, their geometric and optical isomers and mixtures thereof. The patent also discloses the preparation of cis and trans isomers of 2,5 substituted 1,3-oxathiolane derivatives.

U.S. Pat. No. 5,905,082 describes two polymorphic modifications of Lamivudine viz form I and II. Form 1 crystals are short rods or long thin needles with orthorhombic crystal system. Form 1 is a hydrate of Lamivudine consisting of one molecule of water per five molecules of Lamivudine. This form melts at 146° C. (Journal of Chem. Soc., Perkin Trans. 2, page 2655 (1997)). The DSC thermogram (the rate of heating: 2° C./min) of this form shows first an endotherm at 123.6° C. followed by an exotherm at 128° C., finally another endotherm at 179.6° C. This second endotherm is due to conversion of crystal form I to form II, hence form 1 is a metastable crystalline form.

However with rate of heating of 100° C./min form I shows a single endotherm at 146° C., which is it's melting point. The TGA shows a single step sharp weight loss of 2%.

Form I as per U.S. Pat. No. 5,905,082 is prepared by heating a suspension of 64.8 gm Lamivudine in 200 ml water at 45° C. to give a solution and cooling the solution to 30° C. The product crystallizes out as an unstirrable mass. Further breaking this mass and cooling it to 10° C. with stirring and thereafter filtering and drying at 45° C. for 24 hours gives form I crystals.

Form II crystals as disclosed in U.S. Pat. No. 5,905,082 are bipyramidal in shape with tetragonal crystal system. It is an anhydrous form of Lamivudine. This form melts at 177° C. (Journal of Chem. Soc., Perkin Trans. 2, page 2655 (1997)). The DSC thermogram of this form at all scan speeds shows a single peak of endotherm at 177° C. Form II is a stable crystalline form of Lamivudine and is claimed in U.S. Pat. No. 5,905,082.

Form II as per U.S. Pat. No. 5,905,082 is prepared by following procedure: Heat a suspension of 10 gm Lamivudine in 200 ml of industrial methylated spirit to reflux to obtain a clear solution. Filter the solution while hot; distil half the amount of the solvent from the filtrate then stop heating and seed the concentrated solution with authentic form II crystals. The seeded solution is then cooled from 80° C. to 25° C. during one hour. Crystal formation starts at 79° C. Further cooling the suspension to 15° C. and stirring for an hour, filtration, washing with IMS and drying gives Form II crystals.

Crystalline form I have inferior flow property and also lower bulk density, which create problem in handling the product during formulation. In view of the literature cited hereinbefore Lamivudine form I also suffers from stability issues. Therefore, it is desirable to develop a crystalline form of Lamivudine having improved stability and also comparable if not better bioavailability.

When slurried in water both crystal form I and II get converted to another polymorphic form not yet reported in the literature, which is really not a desirable feature for manufacturing practices. Form I converts to form II during milling and formulation operation and because of this the invention embodied in U.S. Pat. No. 5,905,082 for getting form II, a thermodynamically stable polymorph, used for formulation.

The present inventors have surprisingly i found that Lamivudine can also be obtained in a third crystalline form (hereinafter form III), which not only have distinct powder X-ray diffractogram but also have entirely different single crystal X-ray diffraction when compared to form I and II.

OBJECTS OF THE INVENTION

Thus an object of the present invention is to provide a novel crystalline hemihydrate form of Lamivudine with better flow property and bulk density, which enables to have a formulation without any difficulty.

Another object of the present invention is to provide a novel crystalline hemihydrate form of Lamivudine with comparable dissolution rate with the reported polymorphic forms of lamivudine.

Yet another object of the present invention is to provide a novel crystalline form of Lamivudine that is stable during wet granulation using water as a granulating solvent, thereby ensuring the physical stability of the finished solid dosage form.

A further object of the present invention is to provide a process for preparation of novel crystalline hemihydrate of Lamivudine using eco-friendly solvent "water".

Another object of the present invention is to provide suitable pharmaceutical dosage forms of novel crystalline hemihydrate of Lamivudine alone or in combination with other anti HIV agents.

SUMMARY OF INVENTION

Thus in the present invention there is provided a crystalline hemihydrate (form III) of Lamivudine having characteristic powder and single crystal X-ray diffraction as shown in FIGS. 1 and 16 with characteristic 2θ values as given in Table III.

According to another aspect of the present invention there is provided a method for formation of Form III by dissolving Lamivudine in water at 45° C., then cooling the clear solution to 30° C., optionally seeding with form III crystals and further cooling to 10° C. at the rate ranging from 0.5° C./min to 3.5° C./min, isolating the crystals by filtration optionally washing with alcohol and drying at 45-55° C.

DESCRIPTION OF THE INVENTION

As mentioned earlier both form I and form II polymorphs when slurried in water get converted to polymorphic form III, which happens to be thermodynamically stable and does not undergo any change in crystal structure during milling.

This crystal form has been found to have better flow property and higher bulk density in comparison with literature reported forms.

Further study on single crystal X-ray diffraction reveals that it is a hemihydrate form (four molecules of Lamivudine with two molecules of water) of Lamivudine. This product melts at 176-177° C. The DSC thermogram (at the rate of heating=2° C./min) shows first peak of endotherm (Δ H=16.61 J/g) at 100° C. and the second peak of endotherm (Δ H=101.68 J/g) at 179.6°. This crystal form is found to be stable and has better flow property than form 1, and is found to posses comparable bioavailability.

The crystal form III of Lamivudine is obtained by subjecting the hot (45° C.) supersaturated solution of Lamivudine for controlled cooling. Whereas if such solution is cooled suddenly it gives form 1 crystals of Lamivudine.

Figure 6:
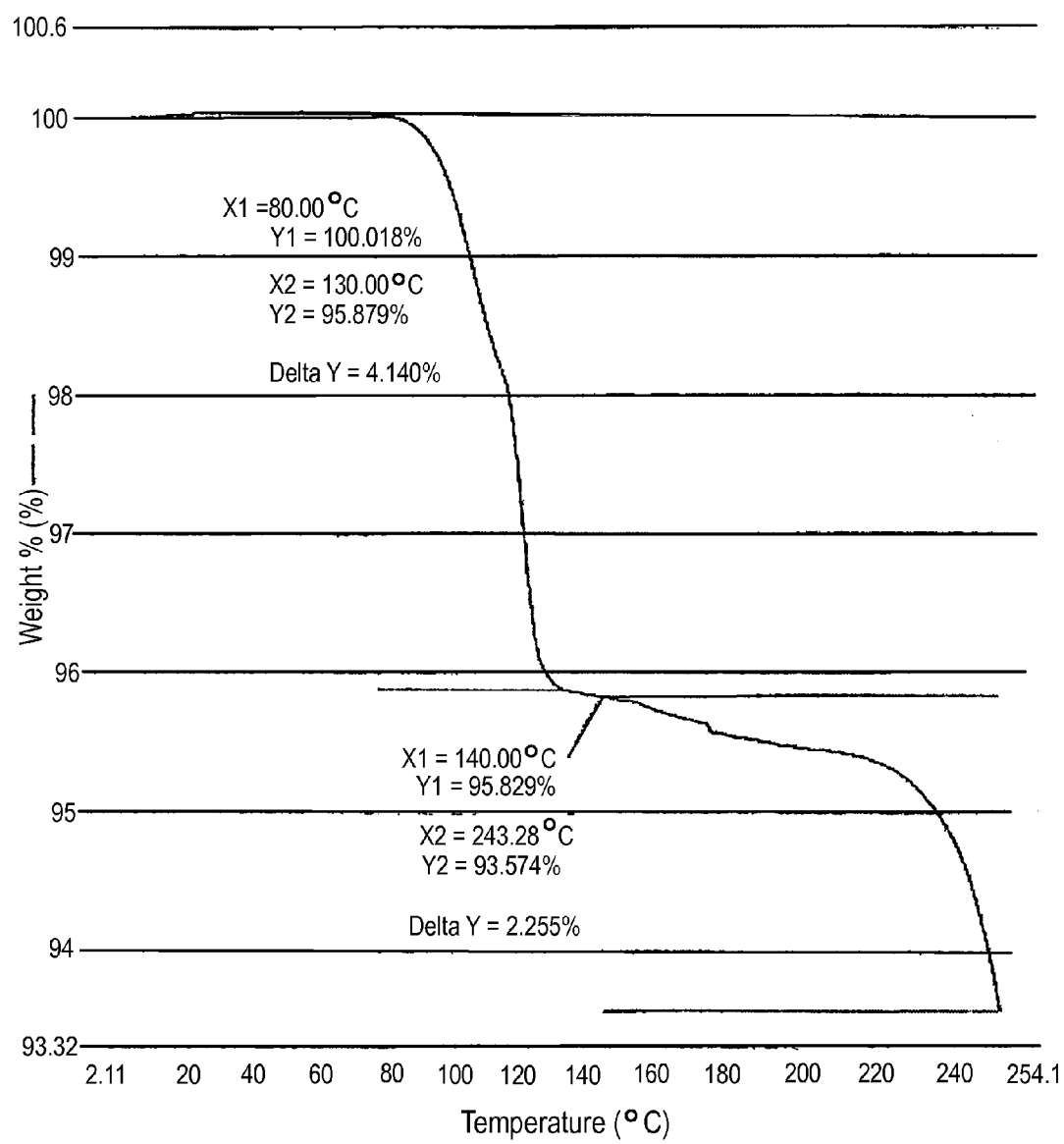

Thermogravimetric analysis (as shown in FIG. 6) of form III crystals of Lamivudine shows 3.5 to 4% single step loss of weight. Moisture content of this crystal form by Karl Fischer titration is in the range of 3.5 to 4.0%, which confirms presence of approximately one mole of water per every two moles of Lamivudine.

Single crystal structure X-ray data (FIG. 16) reveals two molecules of water are associated with four molecules of lamivudine presumably through hydrogen bonds in polymorphic form III. In other words the material of present invention is a hemihydrate having four molecules of lamivudine and two molecules of water. Form III thus obtained has a melting point of 176 to 177° C.

The novel crystalline hemihydrate form (form III) of Lamivudine has better flow property and bulk density, which are important parameters for formulation (Table I).

TABLE I

| Property | Form I | Form II | Form III |
|---|---|---|---|
| Bulk Density (gm/cc) | 0.46 | 0.38 | 0.64 |
| Tap Density (gm/cc) | 0.60 | 0.55 | 0.83 |
| Flow Property (Angle of Repose$) | 33.66° | 32.00° | 32.00° |

$measured as per the procedure provided on page 317 of 'The Theory and Practice of Industrial Pharmacy' by Leon Lachman et al., Third Ed. Varghese Publishing House, Bombay; (1987)

Lamivudine Form I and Form II when slurried in water at ambient temperature for 24 to 48 hours get converted to Form III, which is not at all desirable since during formulation especially in wet granulation such conversion would lead to physical instability of the finished formulation. Hence, use of Lamivudine Form III crystals would certainly have an added advantage over other polymorphic forms mentioned in the literature.

The crystalline form III of Lamivudine as disclosed herein was found to be stable for more than three months when stored at 40±2° C. RH 75±5%.

Comparative thermal analysis data is tabulated in Table II

TABLE II

| Crystal Form | Melting Point | DSC | TGA |
|---|---|---|---|
| I | 135-145° C.<br>124-127° C.*<br>135° C.# | @ 2° C./min: exotherm at 123° then at 177° (FIG. 7)<br>@ 100° C./min: 146° C. (FIG. 8) | One step weight loss between temp 80° C. to 140° C. = 1.52% (FIG. 4) |
| II | 177-178° C.<br>177-178° C.*# | @ 2° C./min and 100° C./min: 177° C. (FIG. 9 & 10) | No weight loss due to crystal bound water. (FIG. 5) |
| III | 176-177° C. | @ 2° C./min first peak at 100° C. and second at 177° C. (FIG. 11)<br>@ 100° C./min: 120° C. (FIG. 12) | One step weight loss between temp 80° C. to 140° C. = 4.14% (FIG. 6) |

The powder X-ray diffraction analysis of form III also shows characteristic 2θ values. Comparative data of 2θ values form III and other literature reported polymorphic forms is provided in Table III

TABLE III

| Form I (FIG. 1) (2θ values) | Form II (FIG. 2) (2θ values) | Form III (FIG. 3) (2θ values) |
|---|---|---|
| 5.20 | 10.70 | 5.50 |
| 6.66 | 12.17 | 7.60 |
| 8.53 | 13.42 | 9.00 |
| 8.81 | 14.30 | 9.62 |
| 9.65 | 14.76 | 10.98 |
| 9.85 | 15.86 | 11.97 |
| 10.15 | 16.83 | 12.52 |
| 10.41 | 17.55 | 12.81 |
| 11.27 | 18.63 | 13.52 |
| 11.38 | 19.68 | 15.19 |
| 11.63 | 20.63 | 15.71 |
| 12.34 | 21.44 | 15.94 |
| 12.60 | 22.13 | 16.57 |
| 12.93 | 22.60 | 16.72 |
| 13.22 | 23.03 | 17.11 |
| 14.60 | 24.44 | 17.57 |
| 15.01 | 24.94 | 17.98 |
| 15.17 | 25.70 | 18.30 |
| 15.67 | 26.51 | 19.26 |
| 15.81 | 27.68 | 19.68 |

TABLE III-continued

| Form I (FIG. 1) (2θ values) | Form II (FIG. 2) (2θ values) | Form III (FIG. 3) (2θ values) |
|---|---|---|
| 16.51 | 28.41 | 20.37 |
| 17.59 | 28.93 | 21.04 |
| 17.98 | 29.72 | 22.00 |
| 18.13 | 30.67 | 22.86 |
| 18.72 | 30.90 | 23.40 |
| 19.10 | 31.30 | 23.70 |
| 19.30 | 31.47 | 24.04 |
| 19.76 | 31.99 | 24.68 |
| 21.788 | 32.40 | 25.15 |
| 23.487 | 32.59 | 26.97 |
| 23.706 | 33.14 | 27.70 |
| 25.44 | 34.01 | 28.74 |
| 25.90 | 35.20 | 30.35 |
| 27.34 | 35.49 | 30.60 |
| 29.46 | 37.27 | 31.94 |
| 31.00 | 38.46 | 33.25 |

The single crystal X-ray diffraction data obtained for form III crystalline form of Lamivudine is tabulated in Table IV Suitable pharmaceutical formulations may conveniently be presented containing predetermined amount of lamivudine in crystalline form III

DESCRIPTION OF ACCOMPANYING FIGURES

FIG. 1: Powder X-ray diffractogram of crystalline form I of Lamivudine.

Figure 2:
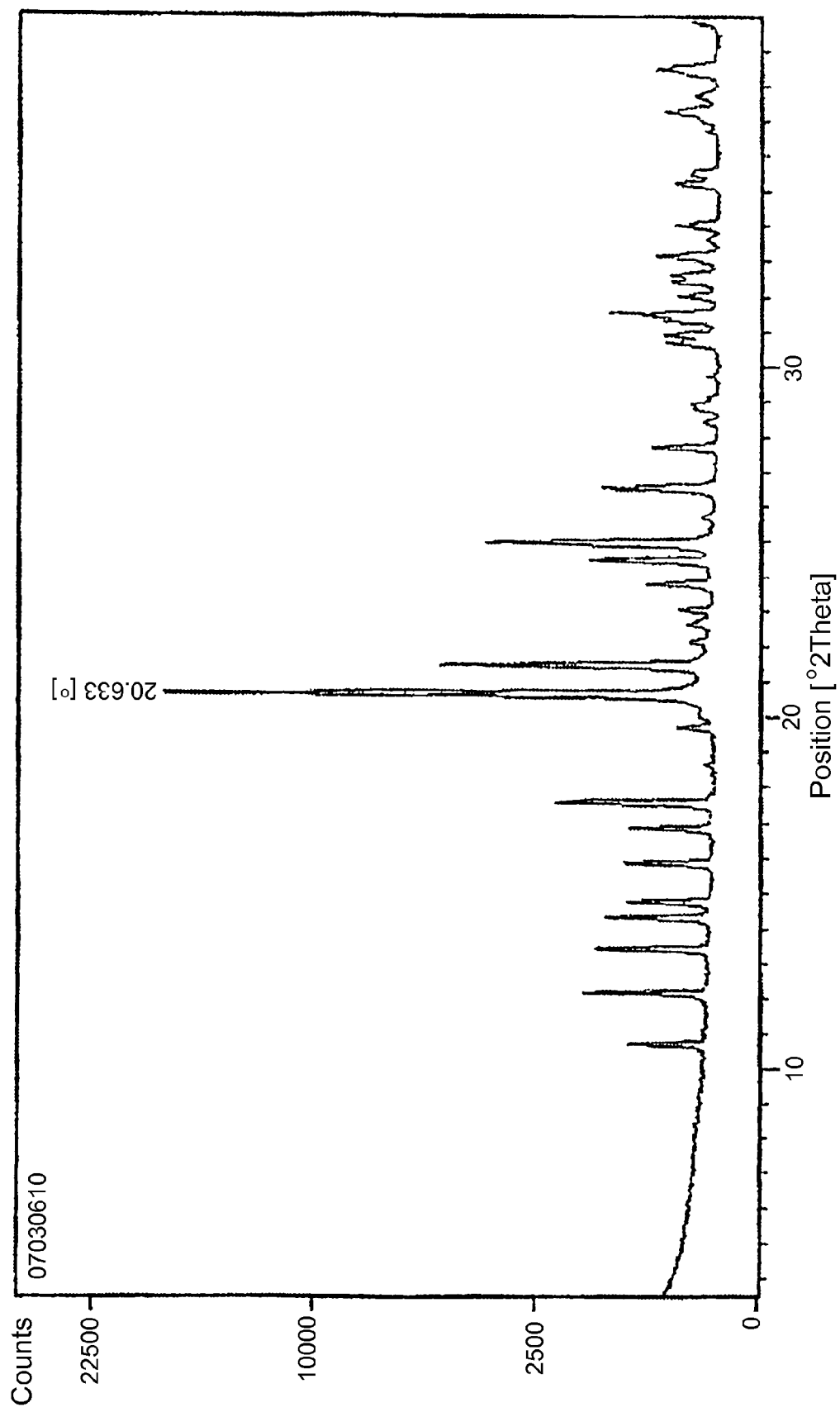

FIG. 2: Powder X-ray diffractogram of crystalline form II of Lamivudine.

Figure 3:
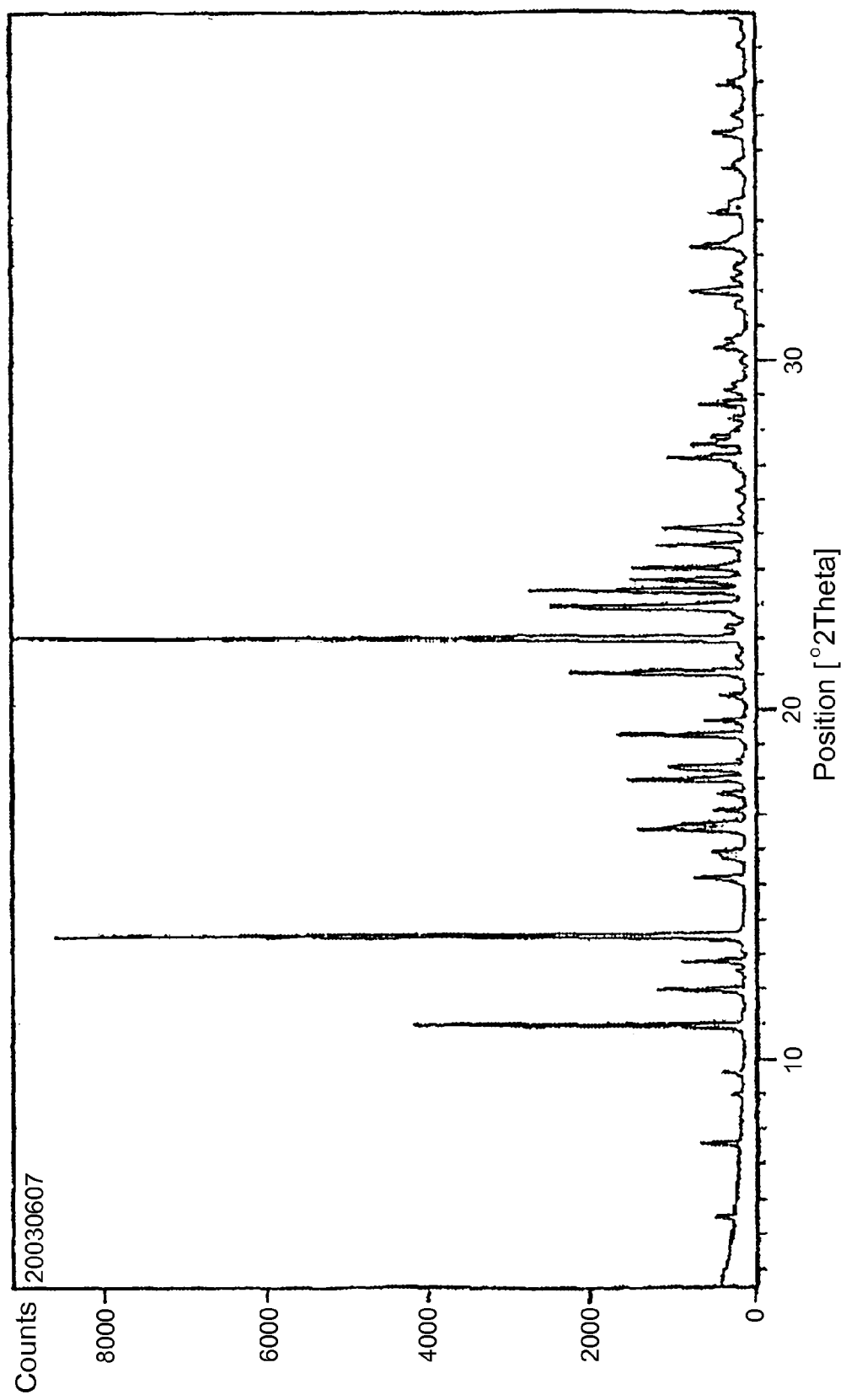

FIG. 3: Powder X-ray diffractogram of crystalline form III of Lamivudine.

Figure 4:
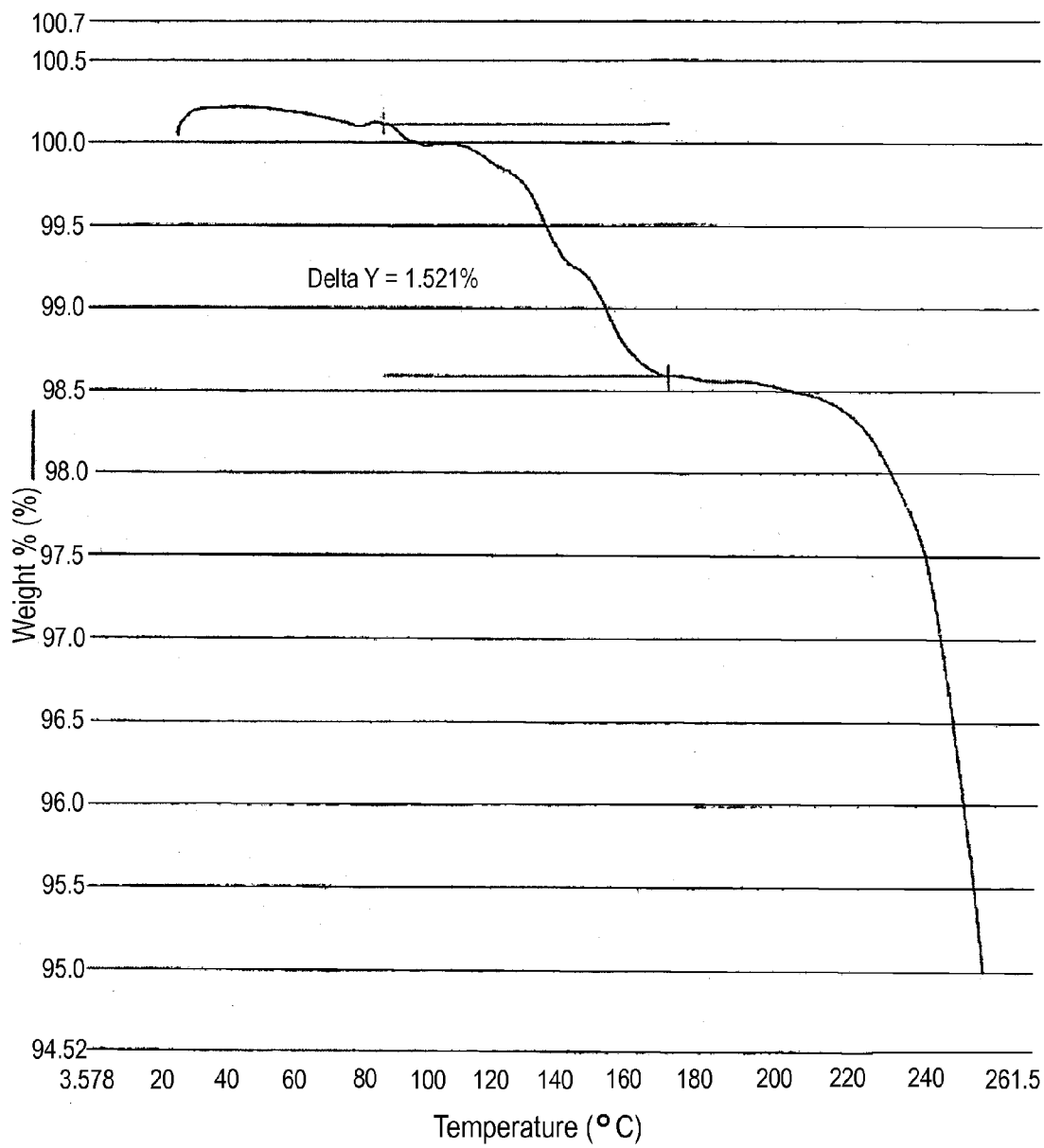

FIG. 4: TGA thermogram of crystalline form I of Lamivudine.

Figure 5:
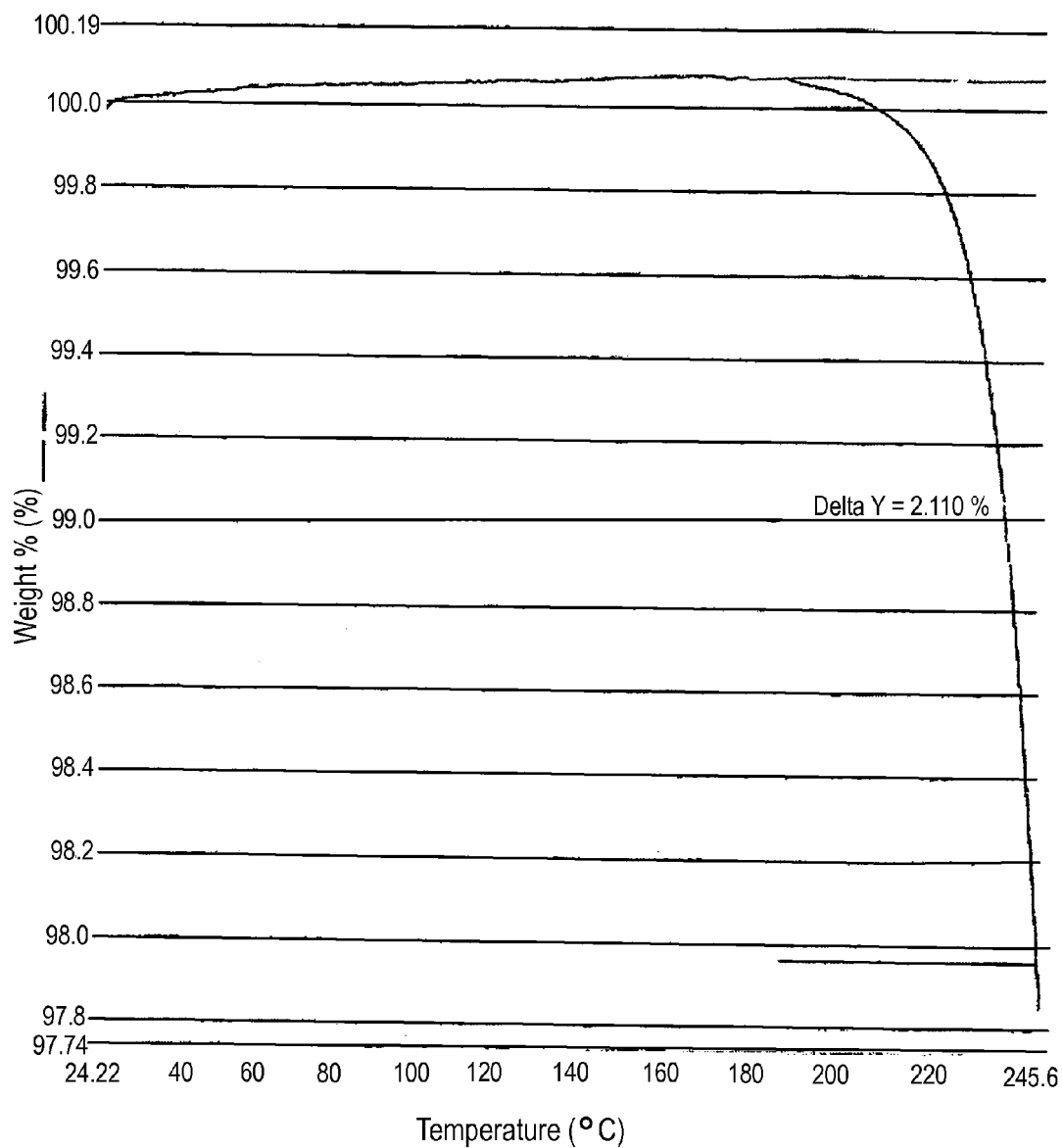

FIG. 5: TGA thermogram of crystalline form II of Lamivudine.

FIG. 6: TGA thermogram of crystalline form III of Lamivudine.

Figure 7:
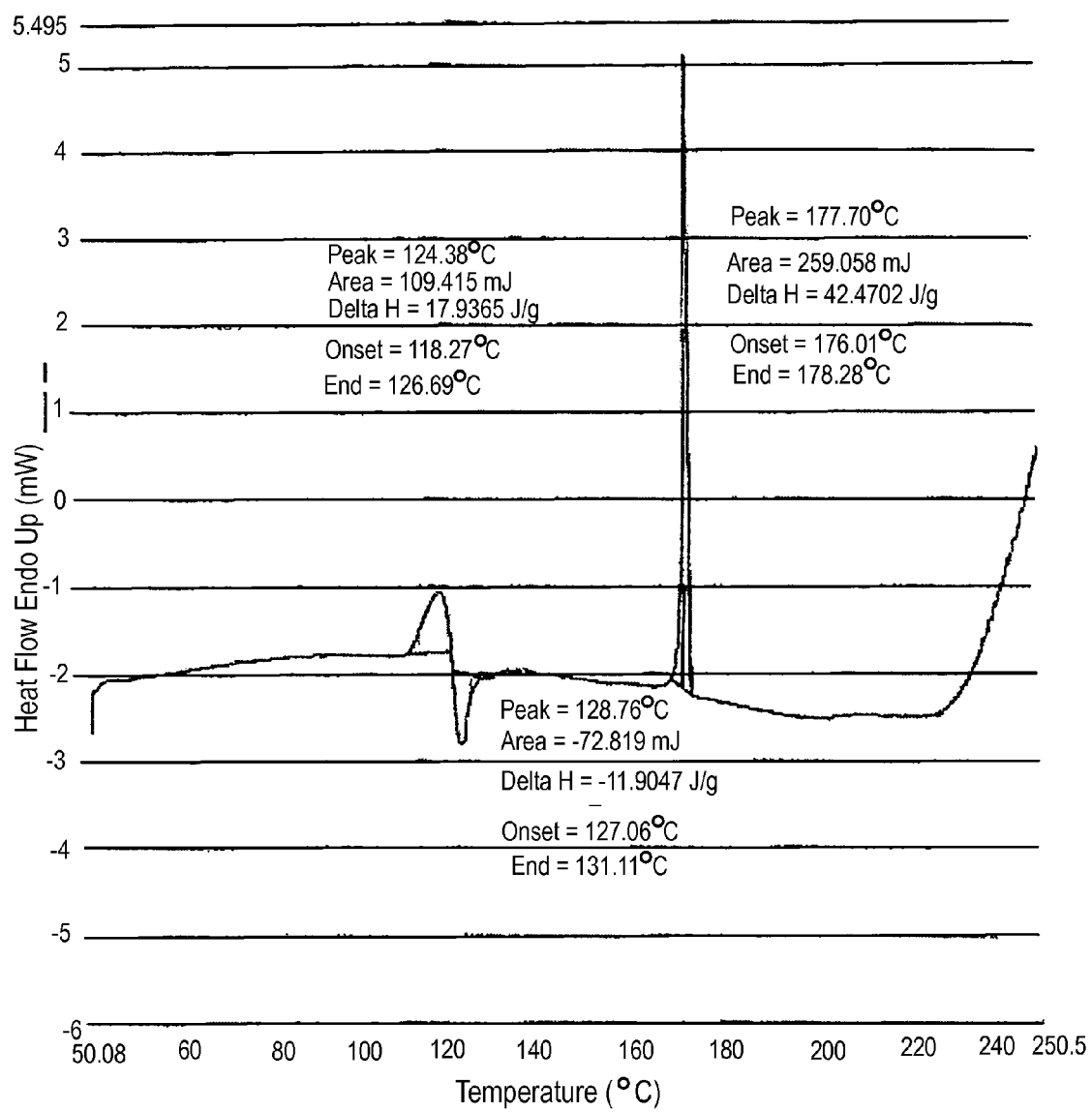

FIG. 7: DSC thermogram of crystalline form I of Lamivudine at heating rate 2° C./min.

Figure 8:
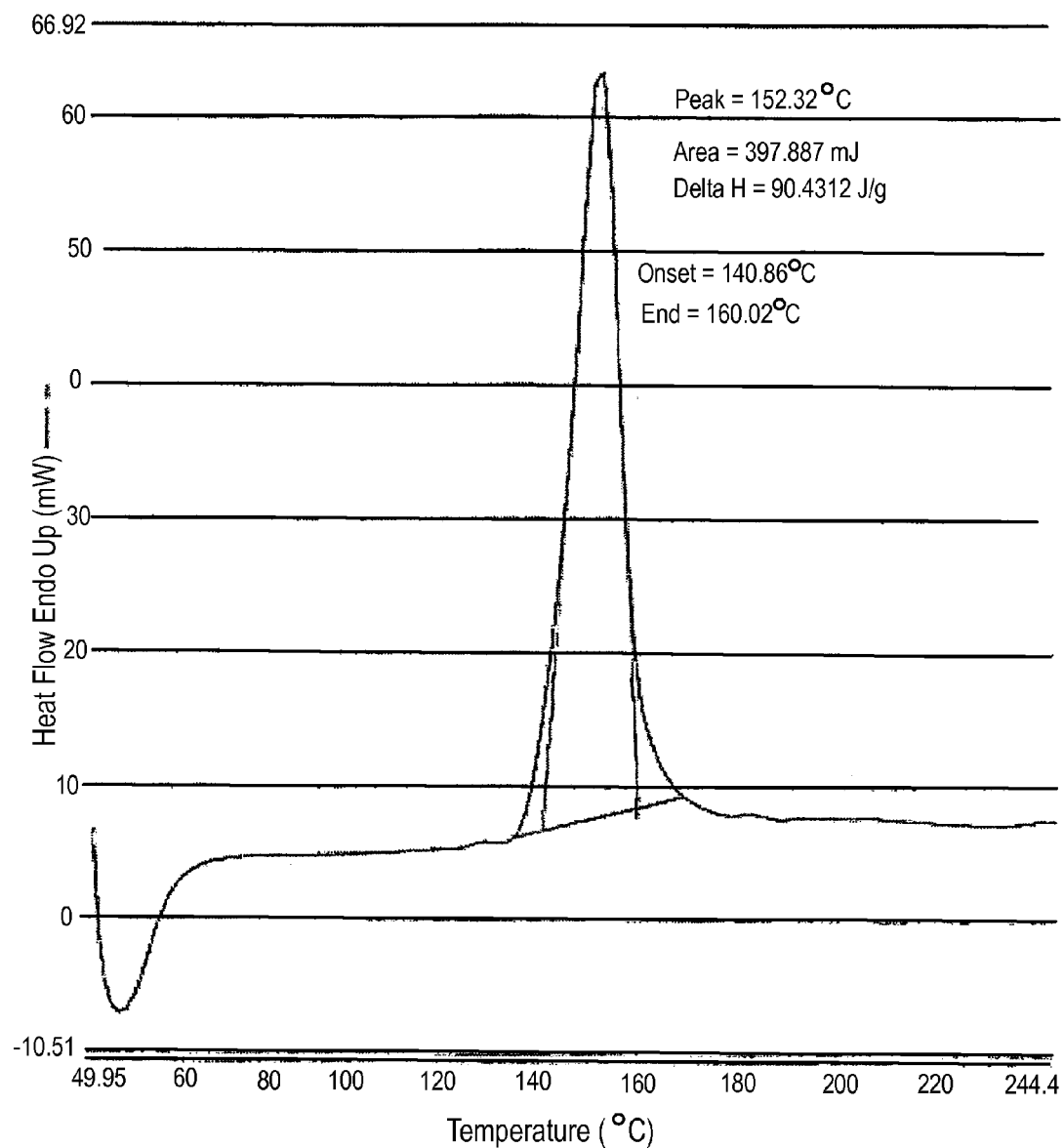

FIG. 8: DSC thermogram of crystalline form I of Lamivudine at heating rate 100° C./min.

Figure 9:
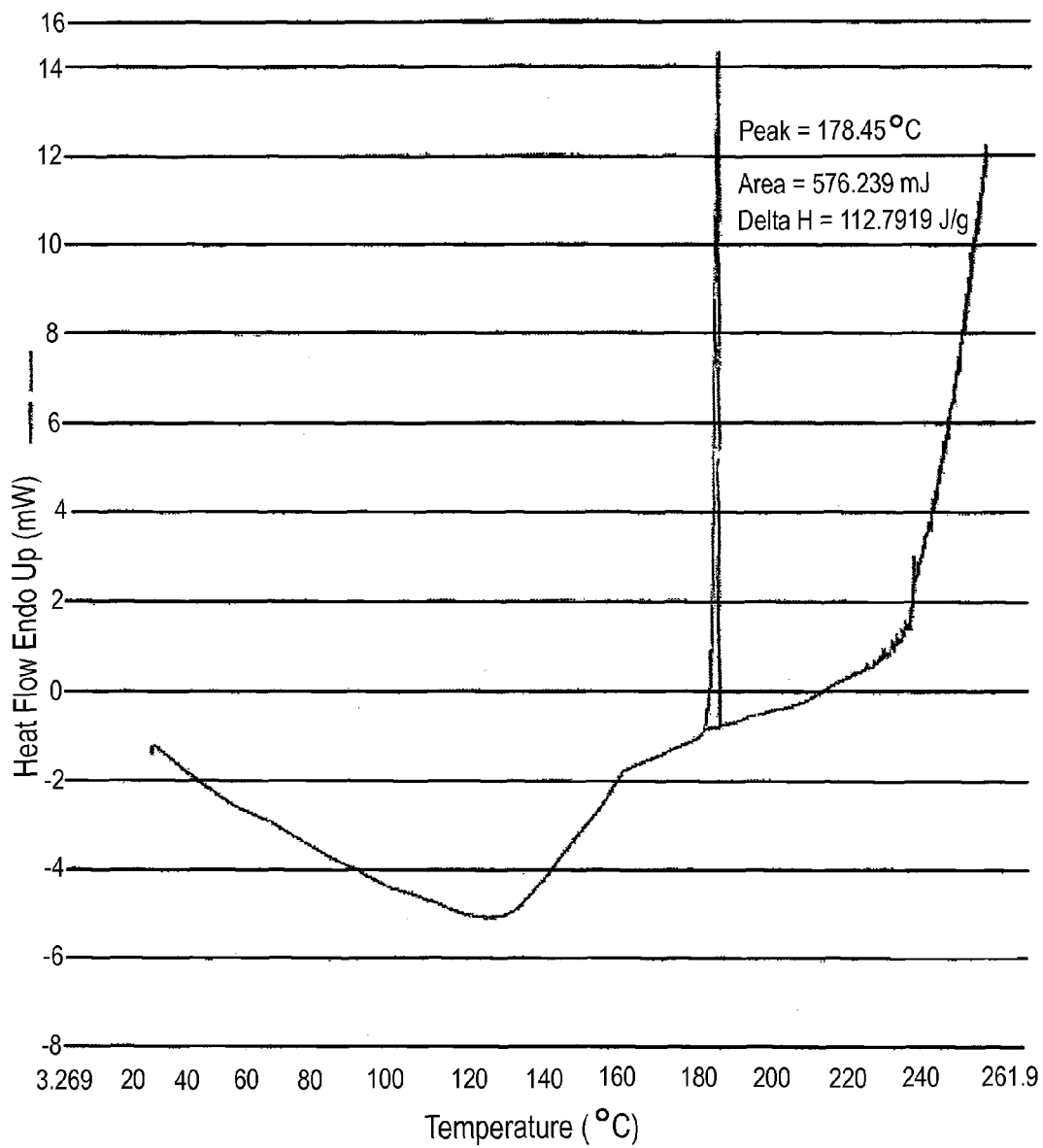

FIG. 9: DSC thermogram of crystalline form II of Lamivudine at heating rate 2° C./min.

Figure 10:
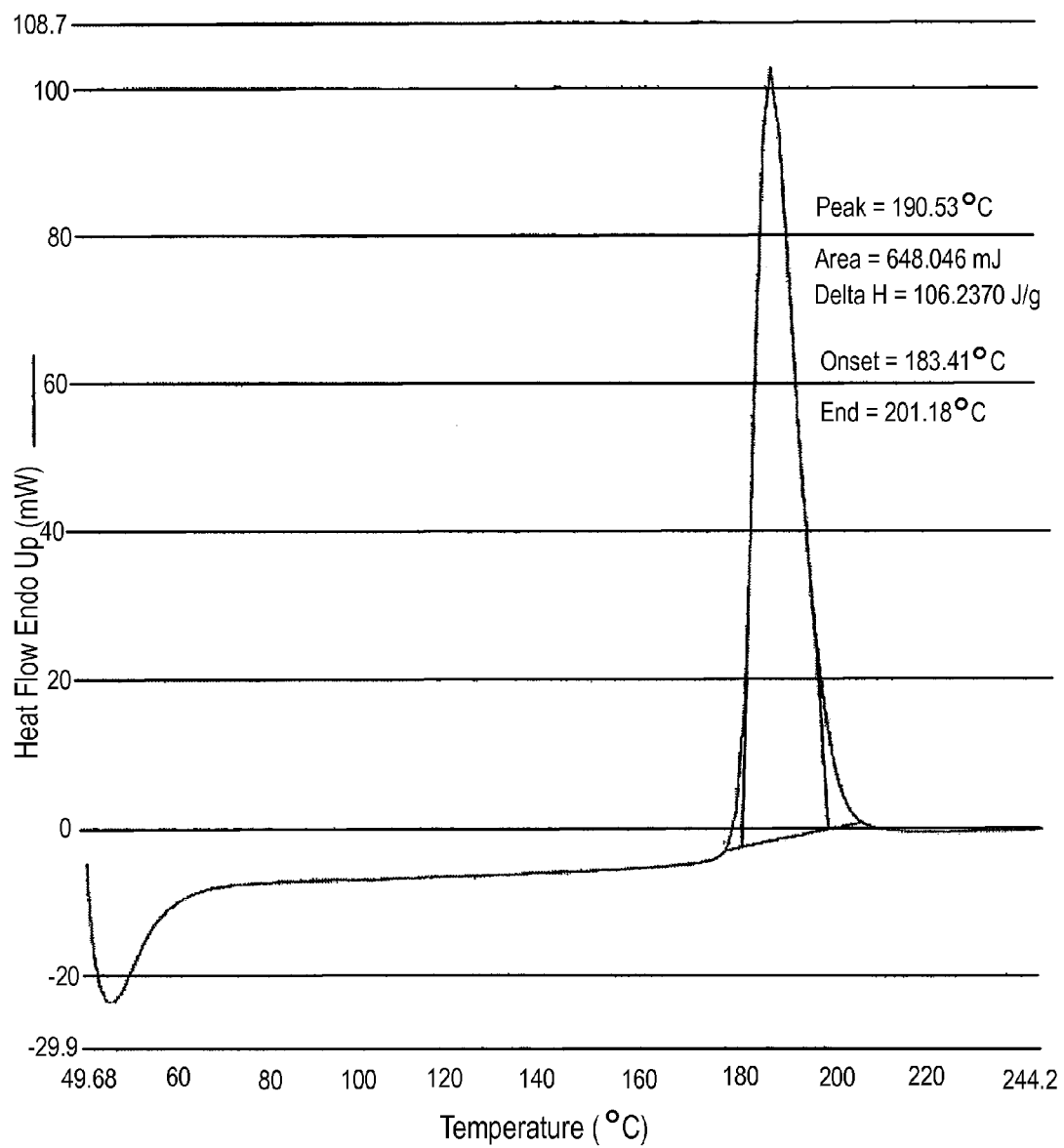

FIG. 10: DSC thermogram of crystalline form II of Lamivudine at heating rate 100° C./min.

Figure 11:
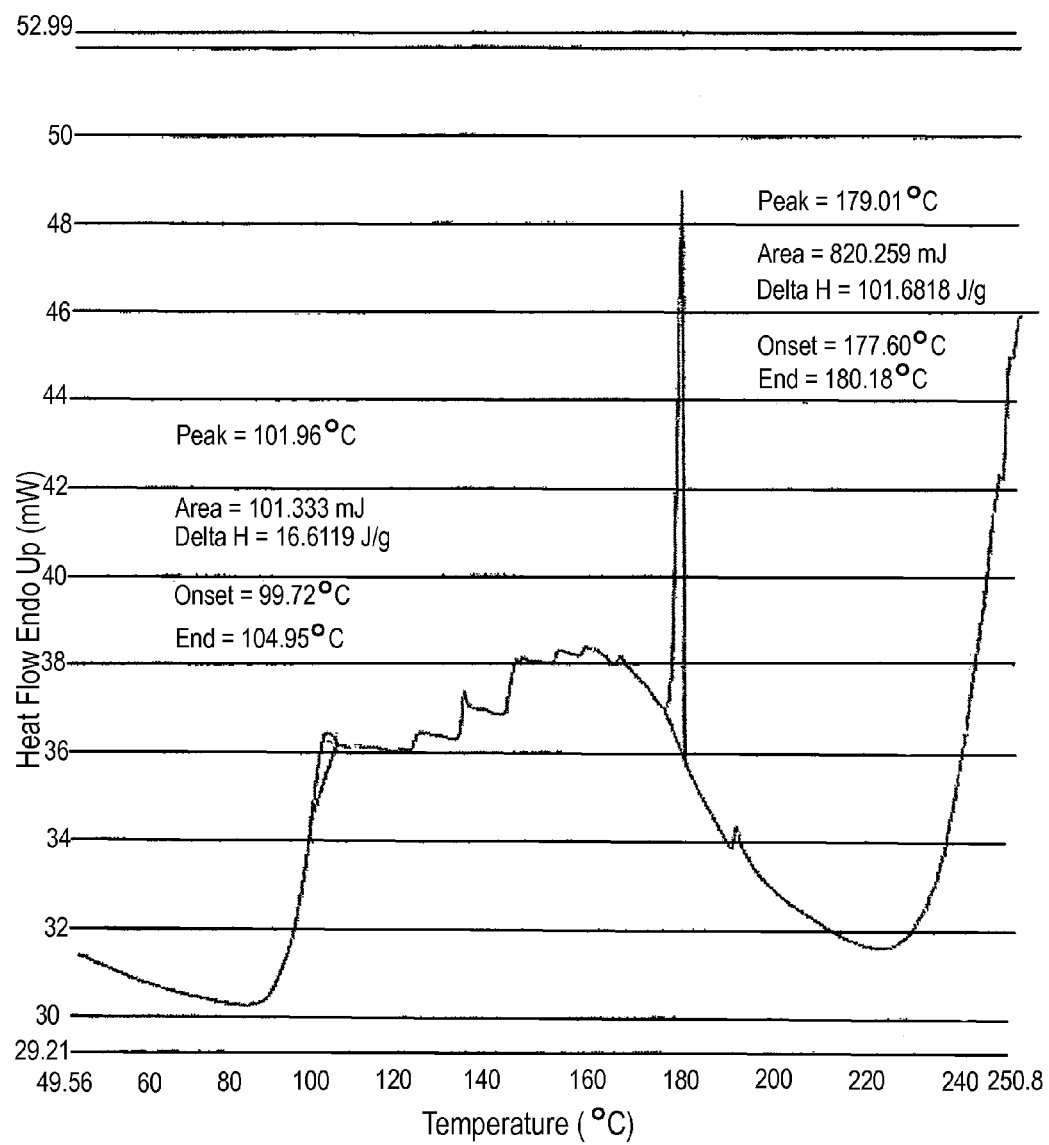

FIG. 11: DSC thermogram of crystalline form III of Lamivudine at heating rate 2° C./min.

Figure 12:
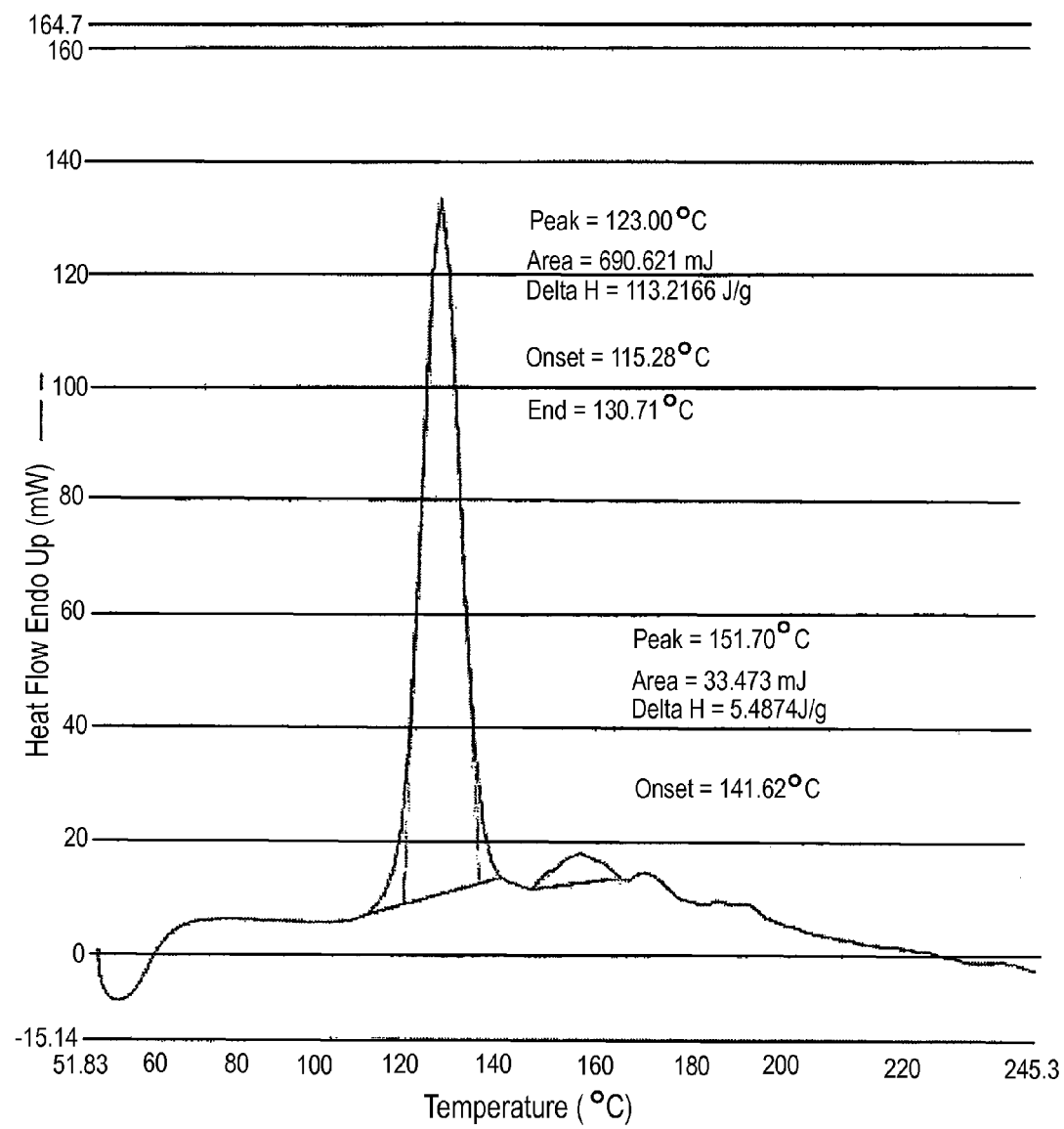

FIG. 12: DSC thermogram of crystalline form III of Lamivudine at heating rate 100° C./min.

Figure 13:
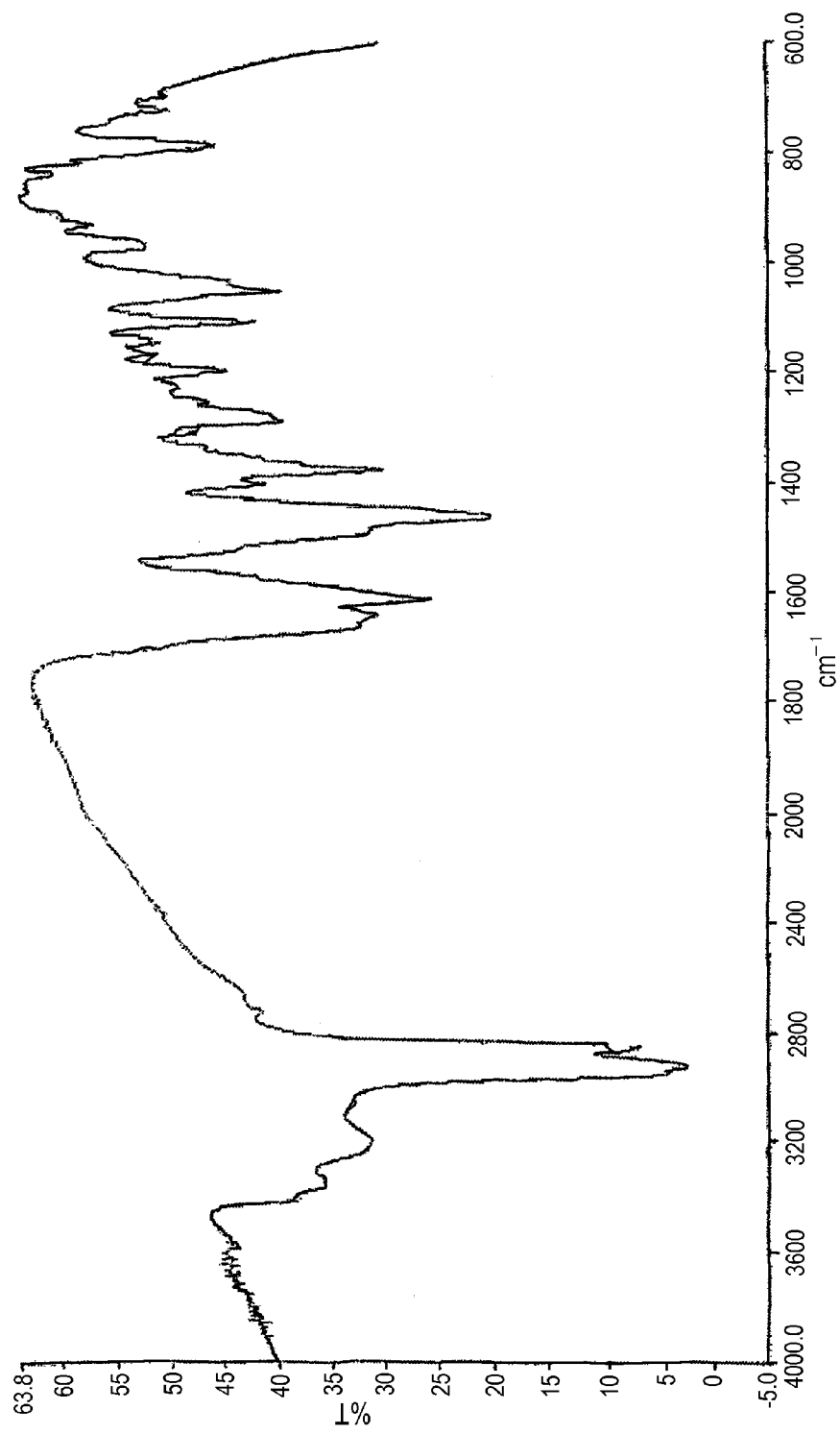

FIG. 13: FTIR spectra of crystalline form I of Lamivudine.

Figure 14:
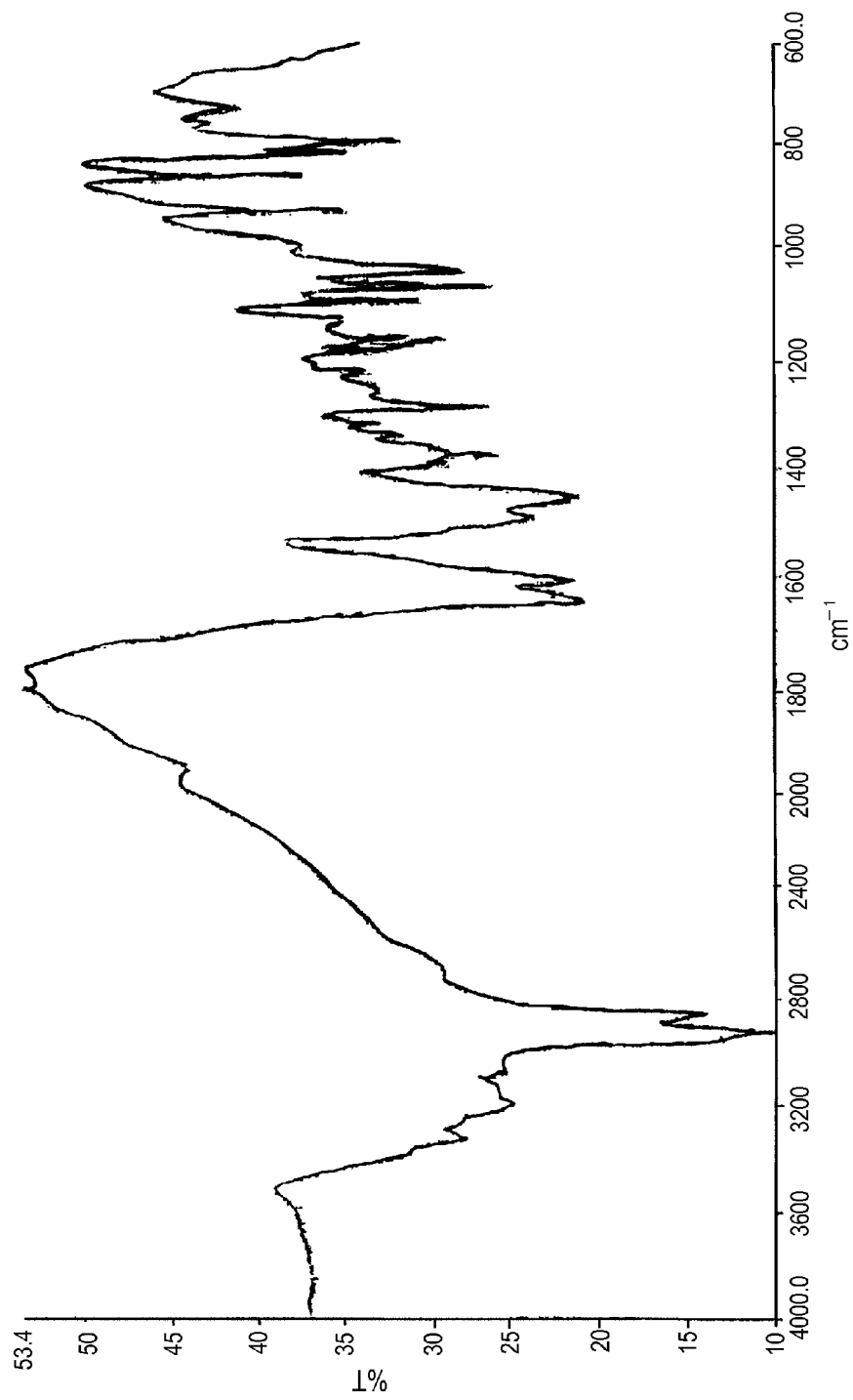

FIG. 14: FTIR spectra of crystalline form II of Lamivudine.

Figure 15:
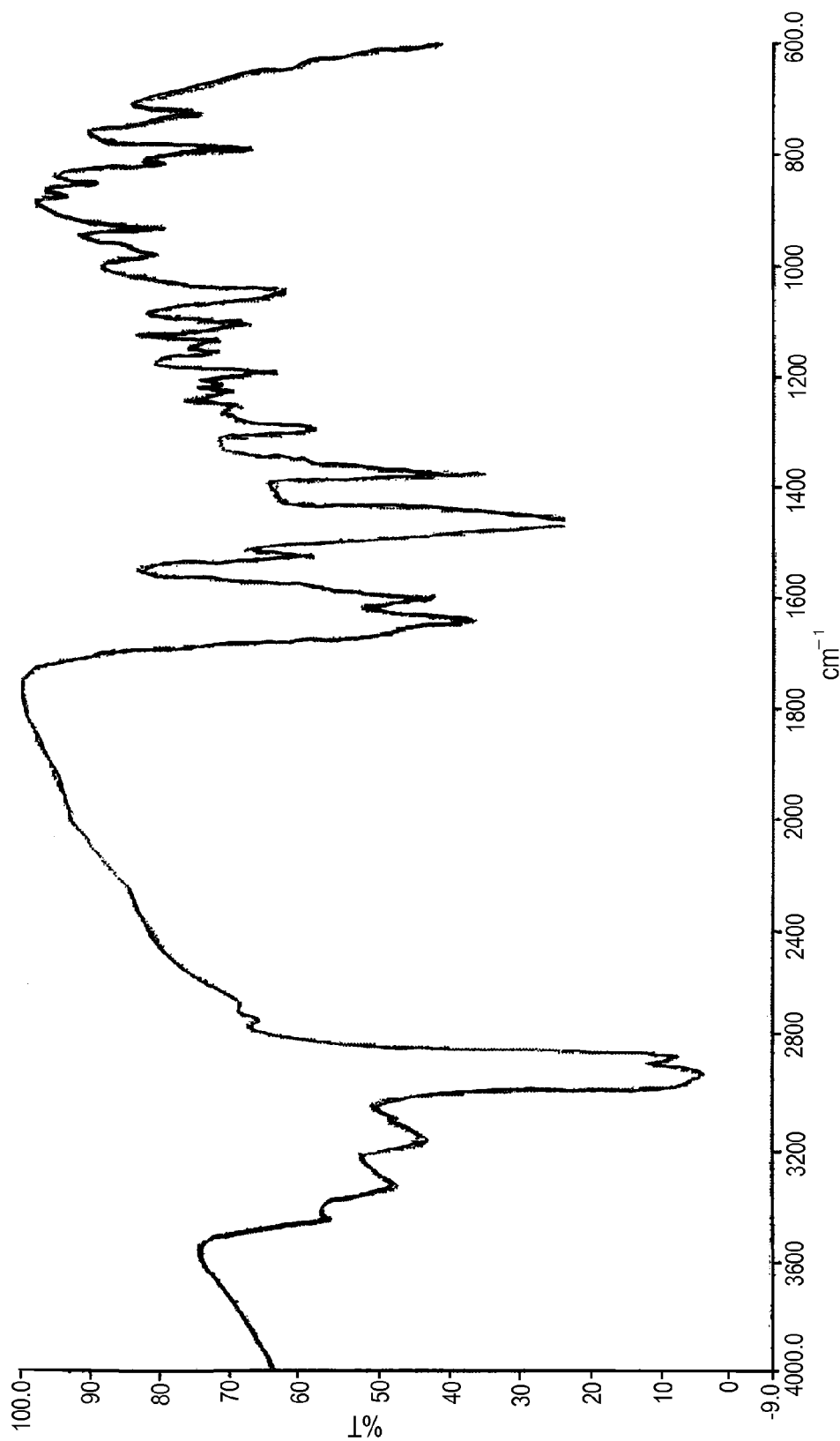

FIG. 15: FTIR spectra of crystalline form III of Lamivudine.

FIG. 16: crystal structure and packing diagram of crystalline form III of Lamivudine obtained by Single crystal X-ray diffraction analysis. (a) Crystal structure of Lamivudine form III. (Disordered atom of minor component S9D1 has been omitted for clarity.) (b) Packing diagram of Lamivudine form III. (Disordered atom of minor component S9D1 has been omitted for clarity.)

The present invention is illustrated in more detail by referring to the following Examples, which are not to be construed as limiting the scope of the invention.

EXAMPLE 1

Preparation of Lamivudine Form III

A suspension of the Lamivudine form-II (25.0) g in water (75.0 ml) was heated to 45° C. in 20 min to give a clear solution. The solution was cooled to 30° C. during a period of 30 min. The crystallization started at 30° C. The mass was further cooled to 10° C. during a period of 20 min and stirred for 1 hour. The product was filtered and washed with ethanol (2×10 ml) then dried in vacuum at 45° C. for 24 hours. Yield=23.0 gms.

IR Spectra [Nujol Mull] (cm$^{-1}$): 3330, 3160, 2923, 2854, 1640, 1600, 1522, 1460, 1376, 1296, 1226, 1193, 1155, 1135, 1106, 1044, 976, 927, 844, 788, 722 (FIG. 15)

X-ray powder diffraction analysis shows peaks at about 5.50, 7.60, 9.00, 9.62, 10.98, 11.97, 12.52, 12.81, 13.52, 15.19, 15.71, 15.94, 16.57, 16.72, 17.11, 17.57, 17.98, 18.30, 19.26, 19.68, 20.37, 21.04, 22.00, 22.86, 23.40, 23.70, 24.04, 24.68, 25.15, 26.97, 27.70, 28.74, 30.35, 30.60, 31.94, 33.25±0.2°2θ.

The single crystal X-ray analysis is carried out using SMART APEX CCD diffractometer by full-matrix least-squares refinement on $F^2$; goodness of fit on $F^2$ was 1.050. A total of 20474 reflections were measured on diffractometer with monochromatised Cu—Kα radiation. The data was collected at θ ranging from 1.26 to 25°. The structure was solved by direct method and the non-hydrogen atoms refined anisotropically. All H atoms were refined isotropically. Refinement converged to give R1=0.0538, wR2=0.1428. Minimum residual electron density was −0.403 e. Å$^{-3}$ and maximum residual electron density was 0.887 Å$^{-3}$. The data is as shown below in Table IV:

TABLE IV

| | | |
|---|---|---|
| Empirical Formula | 2($C_8H_{11}N_3O_3S$)•($H_2O$) | |
| Formula weight | 476.53 | |
| Crystal System | Monoclinic | |
| Space group | P2$_1$ | |
| Unit cell dimensions | a = 11.714 (9) Å | α = 90° |
| | b = 11.214 (9) Å | β = 94.68° |
| | c = 16.197 (12) Å | γ = 90° |
| Z, calculated density | 2, 1.493 Mg/m$^3$. | |
| Cell volume | 2120.4 (3) Å$^3$ | |
| Crystal size | 0.18 × 0.11 × 0.09 | |

Powder pattern generated from single crystal data using MERCURY software was found to be identical to the experimental powder X-ray diffraction pattern of the material of invention (as provided for Form III in Table III and in FIG. 3).

The differential scanning calorimetric analysis at the rate of heating 2° C./min shows first peak of endotherm at 100° C. and second at 177° C. (FIG. 11), and at the rate of heating 100° C./min shows single peak of endotherm at 120° C. (FIG. 12).

The thermogravimetric analysis exhibits one-step weight loss of 4.14% between temp 80° C. to 140° C. (FIG. 6).

EXAMPLE 2

Preparation of Lamivudine Form III

A suspension of the Lamivudine form-II (20.0) g in water (60.0 ml) was heated to 45° C. in 25 min to give a solution.

The solution was cooled to 30° C. in 15 min. The mass was then cooled to 10° C. in 20 min and stirred for 1 h. The product was filtered and washed with IMS (2×10 ml) then dried in vacuum at 45° C. for 24 h. Yield=17 gms.

Powder X-ray diffraction pattern superimposable with that of form III as obtained in Example 1.

EXAMPLE 3

Preparation of Lamivudine Form III

A suspension of the Lamivudine form-II (20.0) g in water (60.0 ml) was heated to 45° C. in 25 min to give a solution. The solution was cooled to 30° C. in 30 min. The mass was then cooled to 10° C. in 20 min and stirred for 1 h. The product was filtered and washed with ethanol (2×10 ml), then dried in vacuum at 45° C. for 24 h. Yield=17 gms.

Powder X-ray diffraction pattern superimposable with that of form III as obtained in Example 1.

EXAMPLE 4

Preparation of Lamivudine Form III

A suspension of the Lamivudine form-II (10.0) g in water (30.0 ml) was heated to 45° C. in 20 min to give a clear solution. The solution was cooled to 30° C. in 15 min. The reaction mass was then cooled to 10° C. in 20 min and stirred for 1 h. The product was filtered and dried in vacuum at 45° C. for 24 h. Yield=8.5 gms.

Powder X-ray diffraction pattern superimposable with that of form III as obtained in Example 1.

EXAMPLE 5

Preparation of Lamivudine Form III

A suspension of the Lamivudine form-1 (10.0) g in water (30.0 ml) was heated to 45° C. in 20 min to give a clear solution. The solution was then cooled to 10° C. in 10 min and stirred for 1 h. The product was filtered and dried in vacuum at 45° C. for 24 h. Yield=7 gms Powder X-ray diffraction pattern superimposable with that of form III as obtained in Example 1.

EXAMPLE 6

Preparation of Lamivudine Form III

A suspension of the Lamivudine form-II (10.0) g in water (30.0 ml) was heated to 45° C. in 20 min to give a clear solution. The solution was then cooled to 10° C. in 10 min and stirred for 1 hr. The product was filtered and dried in vacuum at 45° C. for 24 hr. Yield=8 gm.

Powder X-ray diffraction pattern superimposable with that of form III as obtained in Example 1.

EXAMPLE 7

Preparation of Lamivudine Form III

A suspension of the Lamivudine form-II (50.0) g in water (150.0 ml) was heated to 45° C. in 17 min. to give a clear solution. The solution was cooled slowly to 30° C. in 1.0 hr 40 min. The product was then cooled to 10° C. in 10 min and stirred for 1 h. The product was filtered and dried in vacuum 1.0 mm at 45° C. for 24 h. Yield=44 gm Powder X-ray diffraction pattern superimposable with that of form III as obtained in Example 1.

EXAMPLE 8

Preparation of Lamivudine Form III

A suspension of the Lamivudine form-II (20.0) g in water (80.0 ml) was heated to 45° C. in 25 min to give a clear solution. The solution was cooled slowly to 30° C. in 55 min. The product was then cooled to 10° C. in 5 min and stirred for 1 h at the same temperature. The product was filtered and dried in vacuum for 24 hr at 50-55° C. Yield: 18 gm.

Powder X-ray diffraction pattern superimposable with that of form III as obtained in Example 1.

EXAMPLE 9

Preparation of Lamivudine Form III

A suspension of the Lamivudine form-II (20.0) g in water (100.00) was heated to 45° C. in 25 min to give a clear solution. The solution was cooled slowly to 30° C. in 55 min. The product was then cooled to 10° C. in 5 min and stirred for 1 h at the same temperature. The product was filtered and dried in vacuum for 24 hr at 50-55° C. Yield 18.7 gm.

Powder X-ray diffraction pattern superimposable with that of form III as obtained in Example 1.

EXAMPLE 10

Preparation of Lamivudine Form III

A suspension of lamivudine (Form I or Form II or mixture thereof) (35 gm) in water (105 ml) was heated to 45° C. in 17 minutes to give a clear solution. The solution was cooled slowly to 37° C. in 50 minutes. The solution was seeded with lamivudine form III. The mixture was then cooled to 10° C. in 10 minutes and stirred for one hour. The product was filtered and dried in vacuum at 45° C. for 24 hours. Yield 32 gm.

Powder X-ray diffraction pattern superimposable with that of form III as obtained in Example 1.

EXAMPLE 11

Preparation of Lamivudine Form III

A suspension of the Lamivudine form-II (5.0 gm) in water (5.0 ml) was stirred at 25° C. for 48 hours. The suspension was cooled and stirred at 10° C. for one hour. The product was filtered and then dried under vacuum at 45° C. for 24 hours. Yield=4.5 gms Powder X-ray diffraction pattern superimposable with that of form III as obtained in Example 1.

EXAMPLE 12

Preparation of Lamivudine Form III

A suspension of the Lamivudine form-I (2.0 gm) in water (2.0 ml) was stirred at 25° C. for 24 hours. The suspension was cooled and stirred at 10° C. for one hour. The product was filtered and then dried under vacuum at 45° C. for 24 hours. Yield=1.6 gms Powder X-ray diffraction pattern superimposable with that of form III as obtained in Example 1.

EXAMPLE 13

Preparation of Lamivudine Form I

A suspension of the Lamivudine (10.0) g in water (30.0 ml) was heated to 45° C. in 30 min to give a solution. The solution was cooled to 30° C. in 0.5 min. The product was crystallized as an unstirrable mass. This was broken up and suspension stirred at 10.0° C. for 1 hr. The product was filtered and washed with IMS (2×5 ml) then dried in vacuum at 45° C. for 24 hr. Yield=6.0 gm IR Spectra [Nujol Mull] (cm$^{-1}$): 3356, 3199, 2923, 2854, 1639, 1611, 1461, 1402, 1376, 1309, 1288, 1252, 1196, 1166, 1145, 1107, 1052, 970, 932, 839, 786, 720 (FIG. 13).

X-ray powder diffraction analysis shows peaks at about 5.20, 6.66, 8.53, 8.81, 9.65, 9.85, 10.15, 10.41, 11.27, 11.38, 11.63, 12.34, 12.60, 12.93, 13.22, 14.60, 15.01, 15.17, 15.67, 15.81, 16.51, 17.59, 17.98, 18.13, 18.72, 19.10, 19.30, 19.76, 21.79, 23.49, 23.71, 25.44, 25.90, 27.34, 29.46, 31.00±0.2°2θ.

The differential scanning calorimetric analysis at the rate of heating 2° C./min shows first peak of endotherm at 123° C. and second at 177° C. (FIG. 7), and at the rate of heating 100° C./min shows single peak of endotherm at 146° C. (FIG. 8).

The thermogravimetric analysis exhibits one-step weight loss of 1.52% between temp 80° C. to 140° C. (FIG. 4).

EXAMPLE 14

Preparation of Lamivudine Form I

A suspension of the Lamivudine (250.0 g) in the mixture of water (750.0 ml) and DNS (250.0 ml) was heated to 45° C. in 12 min to give a solution. The solution was cooled to 30° C. in 15 min and seeded with form I crystals. The product was then cooled to 10° C. in 30 min and stirred for 1 h. The product was filtered washed wished with 100 ml water DNS mixture (3:1) and dried in vacuum at 45° C. for 24 h. Yield: 220.0 gm.

Powder X-ray diffraction pattern superimposable with that of form I as obtained in Example 13.

EXAMPLE 15

Preparation of Lamivudine Form II

A suspension of the Lamivudine (10.0) g in ethanol (200.0 ml) was heated to refluxed to give a clear solution. The solution thus formed was subjected to distillation and about 100 ml of ethanol was distilled out at atmospheric pressure. The remaining solution was then cooled to 15° C. in 35 min. The suspension stirred at 15° C. for 1.0 hr. The product was filtered and washed with ethanol (10.0 ml) then dried in vacuum at 50° C. for 12 hr to get 8.2 gm.

IR Spectra [Nujol Mull] (cm$^{-1}$): 3322, 3194, 2950, 2870, 1651, 1611, 1496, 1456, 1396, 1376, 1337, 1316, 1285, 1222, 1180, 1158, 1087, 1058, 1030, 918, 851, 806, 786, 723 (FIG. 14).

X-ray powder diffraction analysis shows peaks at about 10.70, 12.17, 13.42, 14.30, 14.76, 15.86, 16.83, 17.55, 18.63, 19.68, 20.63, 21.44, 22.13, 22.60, 23.03, 24.44, 24.94, 25.70, 26.51, 27.68, 28.41, 28.93, 29.72, 30.67, 30.90, 31.30, 31.47, 31.99, 32.40, 32.59, 33.14, 34.01, 35.20, 35.49, 37.27, 38.46±0.2°2θ.

The differential scanning calorimetric analysis at the rate of heating 2° C./min and 100° C./min shows single peak of endotherm at 177° C. (FIG. 9 and FIG. 10).

The thermogravimetric analysis reveals that it is an anhydrous product. (FIG. 5).

EXAMPLE 12

Pharmaceutical Formulations (a) 150 mg Lamivudine Tablet

| Ingredients per Tablets | Weight (mg.) |
| --- | --- |
| Lamivudine (Form III) | 150 |
| Microcrystalline cellulose NF | 269.62 |
| Sodium starch glycolate NF | 22.50 |
| Colloidal silicon dioxide NF | 2.25 |
| Magnesium Stearate NF | 5.63 |
| Total Weight | 450.00 |

Lamivudine (form III), microcrystalline cellulose, sodium starch glycolate and colloidal silicon dioxide were sieved and blended in octagonal for about 15 minutes. Sieved magnesium stearate was then added and blending continued for a further 2 minutes The blend was compressed in standard tabletting equipment.
Analysis:
Tablet weight: 450 mg±5%
Thickness: 5.0-5.2 mm
Hardness: 150 to 200 N
Disintegration Time: 25 seconds.
% friability: 0.1%.
(b) Lamivudine Form III/Zidovudine Combination Tablets:

| Ingredients per Tablets | Weight (mg.) |
| --- | --- |
| Intra-granular | |
| Lamivudine (Form III) | 150.00 |
| Zidovudine | 300.00 |
| Dicalcium phosphate dihydrate NF | 181.87 |
| Sodium starch glyclolate NF | 56.25 |
| Purified water | Qs |
| Extra-granular | |
| Sodium starch glycolate NF | 18.75 |
| Dicalcium phosphate dihydrate NF | 37.50 |
| Magnessium stearate NF | 5.63 |
| Coating | |
| Opadry YS-1 7706G White | 15 |
| Total Weight | 765.00 |

Lamivudine (form III), Zidovudine, sodium starch glycolate and dicalcium phosphate dihydrate were sieved and mixed in rapid mixer granulator for about 15 minutes. The drymixture obtained was granulated using purified water as granulating agent. The granules were then dried and sifted. Previously sifted sodium starch glycolate and dicalcium phosphate dihydrate blended with the dry granules in octagonal blend for 10 minutes. Previously sifted magnesium stearate was added to this blend and blending continued for further two minutes. The blend was compressed in standard tabletting equipment and then film coated with an aqueous suspension of Opadry YS-1 7706 G White to produce aesthetically acceptable tablets.

Analysis:
Tablet weight: 750 mg±10 mg
Thickness: 5.5-5.6 mm
Hardness: 120 to 130 N
Disintegration Time: 35 seconds (coats), 50 seconds.
% friability: 0.2%.
Dissolution in 0.1 N HCl, 50 rpm, paddle, 900 ml:

| Time (minutes) | Lamivudine (%) | Zidovudine (%) |
|---|---|---|
| 5 | 80.9 | 81.1 |
| 10 | 86.2 | 87.8 |
| 20 | 92.0 | 95.2 |
| 30 | 96.0 | 100.4 |
| 40 | 96.7 | 101.5 |

The invention claimed is:

1. (−) cis-4-amino-1-(2-hydroxymethyl-1,3-oxathiolan-5-yl)-(1H)-pyrimidin-2-one in the form of monoclinic hemihydrate crystals.

2. (−) cis-4-amino-1-(2-hydroxymethyl-1,3-oxathiolan-5-yl)-(1H)-pyrimidin-2-one of claim 1 having a peak of endotherm around 100° C. in a differential scanning calorimetry profile when measured at a heating rate of 2° C. per minute.

3. (−) cis-4-amino-1-(2-hydroxymethyl-1,3-oxathiolan-5-yl)-(1H)-pyrimidin-2-one of claim 1 having a peak of endotherm between 115 and 130° C. in a differential scanning calorimetry profile when measured at a heating rate of 100° C. per minute.

4. (−) cis-4-amino-1-(2-hydroxymethyl-1,3-oxathiolan-5-yl)-(1H)-pyrimidin-2-one of claim 1 showing a weight loss of 4 to 4.5% between the temperatures of 80° and 140° C. in thermogravimetric analysis.

5. (−) cis-4-amino-1-(2-hydroxymethyl-1,3-oxathiolan-5-yl)-(1H)-pyrimidin-2-one of claim 1 having an X-ray diffractometric peak at 2θ (2theta) of 7.6±0.2°.

6. (−) cis-4-amino-1-(2-hydroxymethyl-1,3-oxathiolan-5-yl)-(1H)-pyrimidin-2-one of claim 1 in the form of monoclinic hemihydrate crystals having a bulk density of 0.64 gm/cc.

7. (−) cis-4-amino-1-(2-hydroxymethyl-1,3-oxathiolan-5-yl)-(1H)-pyrimidin-2-one of claim 1 in the form of monoclinic hemihydrate crystals having a tap density of 0.83 gm/cc.

8. (−) cis-4-amino-1-(2-hydroxymethyl-1,3-oxathiolan-5-yl)-(1H)-pyrimidin-2-one of claim 1 having IR peaks at 3160, 2923, 2854, 1640, 1600, 1522, 1296, 1193, 1135, 1106, 1044, 976, 927, and 844 cm$^{-1}$.

9. (−) cis-4-amino-1-(2-hydroxymethyl-1,3-oxathiolan-5-yl)-(1H)-pyrimidin-2-one of claim 8 having IR peaks at 3330, 3160, 2923, 2854, 1640, 1600, 1522, 1460, 1376, 1296, 1226, 1193, 1155, 1135, 1106, 1044, 976, 927, 844, 788, and 722 cm$^{-1}$.

10. (−) cis-4-amino-1-(2-hydroxymethyl-1,3-oxathiolan-5-yl)-(1H)-pyrimidin-2-one of claim 1 having X-ray powder diffraction peaks at 2θ (2theta) of 5.50, 7.60, 9.00, 9.62, 12.52, 12.81, 15.19, 16.57, 17.11, 17.98, 18.30, 19.26, 20.37, 21.04, 23.40, 23.70, 24.04, and 24.68±0.2°.

11. (−) cis-4-amino-1-(2-hydroxymethyl-1,3-oxathiolan-5-yl)-(1H)-pyrimidin-2-one of claim 10 having X-ray powder diffraction peaks at 2θ (2theta) of 5.50, 7.60, 9.00, 9.62, 10.98, 11.97, 12.52, 12.81, 13.52, 15.19, 15.71, 15.94, 16.57, 16.72, 17.11, 17.57, 17.98, 18.30, 19.26, 19.68, 20.37, 21.04, 22.00, 22.86, 23.40, 23.70, 24.04, 24.68, 25.15, 26.97, 27.70, 28.74, 30.35, 30.60, 31.94, and 33.25±0.2°.

12. (−) cis-4-amino-1-(2-hydroxymethyl-1,3-oxathiolan-5-yl)-(1H)-pyrimidin-2-one hemihydrate in the form of monoclinic hemihydrate crystals.

13. (−) cis-4-amino-1-(2-hydroxymethyl-1,3-oxathiolan-5-yl)-(1H)-pyrimidin-2-one of claim 12, wherein the crystals are in isolated or purified form.

14. A pharmaceutical composition comprising a therapeutically effective amount of (−)-cis-4-amino-1-(2-hydroxymethyl-1,3-oxathiolan-5-yl)-(1H)-pyrimidin-2-one in monoclinic hemihydrate crystalline form and a pharmaceutically acceptable carrier therefor, wherein the pharmaceutical composition is in solid dosage form.

15. The pharmaceutical composition according to claim 14 which is an oral dosage form.

16. A pharmaceutical composition comprising a therapeutically effective amount of a combination of 3'-azido-3'-deoxythymidine (AZT) and (−)-cis-4-amino-1-(2-hydroxymethyl-1,3-oxathiolan-5-yl)-(1H)-pyrimidin-2-one in monoclinic hemihydrate crystalline form and a pharmaceutically acceptable carrier, wherein the pharmaceutical composition is in solid dosage form selected from a tablet or a capsule.

17. The pharmaceutical composition according to claim 16 which is a tablet.

18. The pharmaceutical composition according to claim 16 which is a capsule.

19. A process for preparation of monoclinic hemihydrate crystals of (−) cis-4-amino-1-(2-hydroxymethyl-1,3-oxathiolan-5-yl)-(1H)-pyrimidin-2-one, the process comprising dissolving lamivudine in water at a temperature not to exceed 45° C., cooling the solution prior to crystal formation at a rate not exceeding 3.5° C./min under stirring, and separating the resulting monoclinic hemihydrate crystals from mother liquor.

20. The process as claimed in claim 19 wherein the rate of cooling is in the range of 0.5° C./min to 3.5° C./min.

21. The process as claimed in claim 19 further comprising seeding the solution with monoclinic hemihydrate crystals of (−) cis-4-amino-1-(2-hydroxymethyl-1,3-oxathiolan-5-yl)-(1H)-pyrimidin-2-one at 30° C. during cooling.

22. The process as claimed in claim 19 further comprising washing with an organic solvent and drying of the monoclinic hemihydrate crystals wherein the organic solvent is selected from the group consisting of C1 to C4 aliphatic alcohols.

23. The process as claimed in claim 22 wherein the organic solvent is ethanol.

24. The (−) cis-4-amino-1-(2-hydroxymethyl-1,3-oxathiolan-5-yl)-(1H)-pyrimidin-2-one monoclinic hemihydrate crystals formed by the process of claim 19.

25. A process for preparation of monoclinic hemihydrate crystals of (−) cis-4-amino-1-(2-hydroxymethyl-1,3-oxathiolan-5-yl)-(1H)-pyrimidin-2-one, the process comprising stirring lamivudine in the form of orthorhombic crystal form I or tetragonal crystal form II in water at a temperature between 20 to 45° C., cooling the mixture prior to crystal formation under stirring, and separating the resulting monoclinic hemihydrate crystals from mother liquor.

26. The process as claimed in claim 25 further comprising washing with an organic solvent and drying of the monoclinic hemihydrate crystals wherein the organic solvent is selected from C1 to C4 aliphatic alcohols.

27. The process as claimed in claim 26 wherein the organic solvent is ethanol.

28. The method of claim 25, wherein the mixture is cooled at a rate not exceeding 3.5° C./min.

29. The method of claim 28, wherein the rate of cooling is in the range of 0.15° C./min to 0.27° C./min.

* * * * *

30. The method of claim 25, wherein the mixture is cooled slowly.

31. A method of treating HIV infections in humans which comprises administering, separately, simultaneously, or sequentially, to a human in need thereof therapeutically effective amounts of 3'-azido-3'-deoxythymidine (AZT) and (−)-cis-4-amino-1-(2-hydroxymethyl-1,3-oxathiolan-5yl)-(1H)-pyrimidin-2-one (lamivudine) in monoclinic hemihydrate crystalline form.

32. The method according to claim 31 wherein the AZT and lamivudine in monoclinic hemihydrate crystalline form are administered sequentially.

33. The method according to claim 31 wherein the AZT and lamivudine in monoclinic hemihydrate crystalline form are administered simultaneously.

34. The method according to claim 31 wherein the AZT and lamivudine in monoclinic hemihydrate crystalline form are administered orally.

35. The method according to claim 34 wherein the AZT and lamivudine in monoclinic hemihydrate crystalline form are administered as a tablet or tablets.

36. The method according to claim 34 wherein the AZT and lamivudine in monoclinic hemihydrate crystalline form are administered as a capsule or capsules.

37. A method of preparing a pharmaceutical composition comprising admixing (−)-cis-4-amino-1-(2-hydroxymethyl-1,3-oxathiolan-5-yl)-(1H)-pyrimidin-2-one in the form of monoclinic hemihydrate crystals with a pharmaceutically acceptable carrier and shaping the resulting mixture into a solid dosage form.

38. The method according to claim 37 wherein the solid dosage form is a tablet.

39. The method according to claim 38 wherein the solid dosage form is a capsule.

* * * * *

UNITED STATES PATENT AND TRADEMARK OFFICE
CERTIFICATE OF CORRECTION

| | | |
|---|---|---|
| PATENT NO. | : 8,158,607 B2 | Page 1 of 1 |
| APPLICATION NO. | : 12/297174 | |
| DATED | : April 17, 2012 | |
| INVENTOR(S) | : Singh et al. | |

It is certified that error appears in the above-identified patent and that said Letters Patent is hereby corrected as shown below:

Col. 12,
  In claim 19, line 34:

"*" at end of claim should be deleted.

Col. 13,
  In claim 31, line 6:

"340" should read as "3'."

Signed and Sealed this
Thirty-first Day of July, 2012

David J. Kappos
*Director of the United States Patent and Trademark Office*